United States Patent
Mian et al.

(10) Patent No.: US 10,828,439 B2
(45) Date of Patent: Nov. 10, 2020

(54) GAS FLOW INDICATOR

(71) Applicant: Swansea University, Swansea (GB)

(72) Inventors: Omar Mian, Birmingham (GB); Tanwir Muhammed Mian, Llantarnam (GB)

(73) Assignee: Swansea University, Swansea (GB)

( * ) Notice: Subject to any disclaimer, the term of this patent is extended or adjusted under 35 U.S.C. 154(b) by 368 days.

(21) Appl. No.: 15/900,241

(22) Filed: Feb. 20, 2018

(65) Prior Publication Data

US 2018/0256837 A1    Sep. 13, 2018

Related U.S. Application Data

(63) Continuation of application No. 13/642,330, filed as application No. PCT/GB2011/000619 on Apr. 21, 2011, now abandoned.

(30) Foreign Application Priority Data

Apr. 22, 2010    (GB) .................................. 1006736.1

(51) Int. Cl.
*A61M 16/06* (2006.01)
*A61M 16/00* (2006.01)
(Continued)

(52) U.S. Cl.
CPC ........ *A61M 16/0051* (2013.01); *A61M 16/06* (2013.01); *A61M 16/085* (2014.02);
(Continued)

(58) Field of Classification Search
CPC ..... A61B 5/0002; A61B 5/087; A61B 5/0878; A61B 5/097; A61B 5/682; A61M 11/005; A61M 11/06; A61M 11/065; A61M 15/00; A61M 15/0016; A61M 15/0018; A61M 15/0086; A61M 15/009; A61M 16/0051; A61M 16/021; A61M 16/06; A61M 16/0683; A61M 16/0816; A61M 16/0833; A61M 16/085; A61M 16/10; A61M 16/101; A61M 16/12; A61M 16/125; A61M 16/127; A61M 16/16; A61M 2016/0015;
(Continued)

(56) References Cited

U.S. PATENT DOCUMENTS 2,016,212 A    10/1935 O'connell
3,367,324 A    2/1968 Bono
(Continued)

FOREIGN PATENT DOCUMENTS

WO    WO-1997010018 A1    3/1997

OTHER PUBLICATIONS

"U.S. Appl. No. 13/642,330, Final Office Action dated Mar. 31, 2016", 14 pgs.
(Continued)

*Primary Examiner* — Annette Dixon
(74) *Attorney, Agent, or Firm* — Klarquist Sparkman, LLP (57) ABSTRACT

A gas flow indicator for medical equipment is described which is configured to provide an audible indication of gas flow. The medical equipment may be in the form of a respiratory care device, an airway management device, a heat moisture exchanger, an oxygen enrichment device or a breathing mask.

18 Claims, 5 Drawing Sheets

(51) Int. Cl.
*A61M 16/08* (2006.01)
*A61M 16/10* (2006.01)

(52) U.S. Cl.
CPC ...... *A61M 16/0875* (2013.01); *A61M 16/101* (2014.02); *A61M 16/1045* (2013.01); *A61M 2016/003* (2013.01); *A61M 2205/183* (2013.01); *A61M 2205/186* (2013.01); *A61M 2205/43* (2013.01); *A61M 2205/44* (2013.01); *A61M 2205/581* (2013.01)

(58) Field of Classification Search
CPC .... A61M 2016/003; A61M 2205/0227; A61M 2205/43; A61M 2205/581; A61M 2205/583; A61M 2205/59; A61M 2206/14; A61M 2230/432; G10K 5/00; Y10T 137/87627
See application file for complete search history.

(56) References Cited

U.S. PATENT DOCUMENTS

| | | | |
|---|---|---|---|
| 3,794,072 A * | 2/1974 | Diedrich | A61M 16/06 137/893 |
| 3,837,341 A | 9/1974 | Bell | |
| 3,894,537 A * | 7/1975 | Camp | A61M 11/06 128/203.17 |
| 3,906,996 A | 9/1975 | Depass et al. | |
| 4,602,644 A | 7/1986 | Dibenedetto et al. | |
| 5,320,092 A | 6/1994 | Ryder | |
| 5,451,190 A | 9/1995 | Liardet | |
| 5,690,097 A | 11/1997 | Howard et al. | |
| 5,724,959 A | 3/1998 | Mcaughey et al. | |
| 5,816,186 A * | 10/1998 | Shepherd | G10K 5/00 116/137 R |
| 5,857,460 A * | 1/1999 | Popitz | A61M 16/06 128/204.22 |
| 6,039,042 A | 3/2000 | Sladek | |
| 6,578,571 B1 * | 6/2003 | Watt | A61M 15/0016 128/200.14 |
| 6,679,432 B1 | 1/2004 | Arnold | |
| 6,718,969 B1 * | 4/2004 | Rubin | A61M 15/0086 128/200.14 |
| 7,089,932 B2 * | 8/2006 | Dodds | A61B 5/0002 128/202.22 |
| 7,418,962 B1 | 9/2008 | Rao | |
| 2003/0041859 A1 * | 3/2003 | Abrams | A61M 16/101 128/200.22 |
| 2006/0117856 A1 | 6/2006 | Orr et al. | |
| 2007/0227360 A1 | 10/2007 | Atlas et al. | |
| 2008/0087287 A1 | 4/2008 | Ging et al. | |
| 2008/0092898 A1 | 4/2008 | Schneider et al. | |
| 2013/0068221 A1 | 3/2013 | Mian et al. | |

OTHER PUBLICATIONS

"U.S. Appl. No. 13/642,330, Final Office Action dated Sep. 21, 2017", 18 pgs.
"U.S. Appl. No. 13/642,330, Non Final Office Action dated Apr. 19, 2017", 10 pgs.
"U.S. Appl. No. 13/642,330, Non Final Office Action dated Jul. 6, 2015", 13 pgs.
"U.S. Appl. No. 13/642,330, Preliminary Amendment filed Oct. 19, 2012", 5 pgs.
"U.S. Appl. No. 13/642,330, Response filed Jun. 27, 2016 to Final Office Action dated Mar. 31, 2016", 12 pgs.
"U.S. Appl. No. 13/642,330, Response filed Aug. 22, 2017 to Non Final Office Action dated Apr. 19, 2017", 8 pgs.
"U.S. Appl. No. 13/642,330, Response filed Dec. 7, 2015 to Non Final Office Action dated Jul. 6, 2015", 9 pgs.
"International Application No. PCT/GB2011/000619, International Search Report dated Dec. 9, 2011", (Dec. 9, 2011), 7 pgs.
U.S. Appl. No. 13/642,330, filed Dec. 4, 2012, Gas Flow Indicator.

* cited by examiner

GAS FLOW INDICATOR

PRIORITY CLAIM TO RELATED APPLICATIONS

This application is a continuation and claims the benefit of priority to U.S. application Ser. No. 13/642,330, filed Dec. 4, 2012, which is a national stage application under 35 U.S.C. § 371 of PCT/GB2011/000619, filed Apr. 21, 2011, and published as WO 2011/131942 A2 on Oct. 27, 2011, which claims priority to United Kingdom Application No. 1006736.1, filed Apr. 22, 2010, which applications and publication are incorporated by reference as if reproduced herein and made a part hereof in their entirety, and the benefit of priority of each of which is claimed herein.

FIELD OF THE INVENTION

This invention relates to a gas flow indicator. Particularly, but not exclusively, the invention relates to a gas flow indicator for use in medical equipment such as that employed in respiratory care and airway management (for example, in equipment used for the delivery of gases to and from a patient).

BACKGROUND TO THE INVENTION

There are many instances when it is desirable to monitor a patient's breathing and/or the gases they are inhaling or exhaling. For example, a patient may be administered with a general anaesthetic prior to a surgical procedure. In this case, the anaesthetic may be provided in the form of a gas which is delivered to the patient through a mask or tube inserted via the patient's mouth or nose and into their trachea. In some cases, patients are anaesthetised in an anaesthetic room before being transferred to a separate surgical theatre and so it is necessary for the patient to be disconnected from the anaesthetic equipment in the anaesthetic room and reconnected to the anaesthetic equipment in the theatre.

Disposable heat moisture exchangers (HME's) are commonly used to warm and humidify otherwise cold gases before they pass into a patient's lungs. Thus, effectively, an HME serves as an artificial nose in circumstances where gases are being delivered to a patient through tubes or masks which are arranged to bypass the nose. Typically, an HME will include a gas inlet for connection to a gas supply, a gas outlet for connection to an endotracheal tube or laryngeal mask, and a filter therebetween. The filter serves to trap heat and moisture exhaled from the patient's lungs and enables incoming gases to return this heat and moisture to the patient's lungs on inhalation. HME's typically also include a sampling port through which an anaesthetist can monitor the concentration and flow rate of the gases being supplied to the patient. For example, they may monitor the amount of oxygen and/or anaesthetic being delivered to the patient. Usually, the gases will be monitored through the sampling port when the patent is in the anaesthetic room and then the monitoring equipment will be disconnected from the sampling port to allow the patent to be transferred to the theatre. Once in theatre, the sampling port may be reconnected to further monitoring equipment or it may simply be closed off by a cap. However, it is not uncommon for an anaesthetist to forget to reconnect or close the sampling port, causing gases to escape from the open sampling port so that the patient is not effectively ventilated.

It is also common to use a disposable oxygen enrichment device to provide a patient with a higher than normal concentration (e.g. 50%) of oxygen in the air that they breath, when transferring the patient from theatre to a post-operative recovery room. Such a device is usually connected to a portable oxygen cylinder and typically comprises a reservoir configured to receive oxygen flowing from the cylinder through a first inlet, a second inlet which is open to the air and an outlet arranged to provide a mixture of air and oxygen from the reservoir to the patient through a suitable tube or mask. The reservoir is sometimes configured as a rigid component that is shaped like a cigar or it may be constituted by a flexible bag such as in patent application PCT/AU96/00417. An advantage of using a flexible bag as the reservoir is that the bag will deflate and inflate to provide a visible indication that the patient is breathing (i.e. inhaling and exhaling). However, if the oxygen cylinder is empty, disconnected or delivering oxygen at an incorrect flow rate, the patient may still be breathing regularly (and the bag inflating and deflating accordingly) but they will not be receiving the required level of oxygen. Moreover, they may, in fact, be re-breathing their own expressed air which is highly undesirable since it results in the patient obtaining progressively decreasing concentrations of oxygen and progressively increasing concentrations of carbon dioxide.

It is therefore an aim of the present invention to provide a gas flow indicator that addresses the above-mentioned problems.

SUMMARY OF THE INVENTION

According to a first aspect of the present invention there is provided a gas flow indicator for medical equipment configured to provide an audible indication of gas flow.

Embodiments of the present invention therefore provide a simple and effective mechanism for quickly detecting if gas is flowing as it should through medical equipment. Importantly, any person monitoring the gas flow need not look at the gas flow indicator in order to know whether or not the gas is flowing as it should. Instead, those people may be busy with other tasks, safe in the knowledge that they will be alerted to any potential problems by an audible sound (or lack thereof). Moreover, the audible sound generated by the gas flow indicator will enable a listener to quickly detect the location of a potential problem by following the sound to its source.

The gas flow indictor may be arranged to indicate correct gas flow to a patient or it may be arranged to indicate incorrect gas flow—for example, when gas is escaping and not reaching the patient. Thus, depending on the arrangement of the gas flow indicator, the presence of an audible sound may signal correct gas flow and the absence of an audible sound may signal incorrect gas flow (e.g. to indicate that the patient is not breathing). Alternatively, the absence of an audible sound may signal correct gas flow and the presence of an audible sound may signal incorrect gas flow (e.g. to indicate that gas is escaping).

The medical equipment may be configured for respiratory care and/or airway management.

In embodiments of the present invention, the gas flow indicator may be provided in medical equipment disposed close to a patient's air inlet so as to indicate if there is a problem with the gases getting to the patient.

The gas flow indicator may disposable.

The gas flow indicator may be configured for retro-fitting to existing medical equipment. Alternatively, the gas flow indicator may integrally formed with the medical equipment.

The audible indication may be provided by a whistling means. The whistling means may comprise an occlusion arranged to force gas through a narrow opening to create an audible sound. Alternatively, the whistling means may comprise a blade configured to bisect a flow of gas, thereby creating a turbulent vortex which causes the gas to vibrate to make an audible sound. The whistling means may further comprise a chamber in which the gas may resonate. The chamber may be configured such that the gas resonates therein at a pre-determined frequency. The whistling means may further comprise a ball or other structure arranged to rattle in the gas flow.

The gas flow indicator may be configured to maintain an audible indication of gas flow at all times when the medical equipment is in use. Accordingly, the gas flow indicator will serve as an additional safety feature to reassure listeners that gas is flowing through the medical equipment as intended. Of course, in this instance, the absence of the audible indication at any point during use will denote that gas is not flowing as intended.

In particular embodiments, the medical equipment may be constituted by a heat moisture exchanger (HME). The heat moisture exchanger may comprise an inlet for connection to a gas supply, an outlet for connection to an endotracheal tube or laryngeal mask, and a filter therebetween. The filter may be configured to trap heat and moisture on exhalation and to return heat and moisture on inhalation. The heat moisture exchanger may further comprise a sampling port. The gas flow indicator may be configured for use in one or more of the inlet, the outlet or the sampling port of the heat moisture exchanger. In one embodiment, the gas flow indicator may be arranged to provide an audible indication when gas is escaping through the sampling port (i.e. when the sampling port has not been closed off or reconnected to monitoring equipment).

In other embodiments, the medical equipment may be constituted by an oxygen enrichment device. The oxygen enrichment device may comprise a reservoir configured to receive oxygen flowing from an oxygen cylinder through a first inlet, a second inlet which is open to the air and an outlet arranged to provide a mixture of air from the second inlet and oxygen from the reservoir to the patient through a suitable tube or mask. The reservoir may be configured as a rigid (e.g. cigar-shaped) component or a flexible component, such as a bag. The gas flow indicator may be located in the first inlet and may be arranged to provide an audible indication when gas is correctly flowing from the cylinder into the reservoir. Accordingly, the lack of an audible sound will indicate that there is a problem with the oxygen supply. For example, the cylinder may be empty (which happens quite often since relatively small cylinders are employed to make them easily portable), or the cylinder may not have been set correctly (e.g. the gas supply may be turned off or not set to deliver the desired flow rate). In each of the above cases, the result is that not enough oxygen is flowing into the reservoir for inhalation by the patient. As a consequence, the patient will be breathing in a hypoxic mixture not containing sufficient oxygen. Moreover, the patient may be re-breathing their own expressed air containing progressively decreasing concentrations of oxygen and progressively increasing concentrations of carbon dioxide. Thus, the gas flow indicator in this embodiment can quickly alert staff to the fact there is a problem with the oxygen supply even if the bag is inflating and deflating, as expected.

In certain embodiments, the gas flow indicator may be configured only to provide an audible sound when gas is flowing at a pre-determined flow rate. For example, it may desirable to provide a patient with a 50% mixture of air and oxygen, and this might be achievable with an oxygen supply set to provide 3 litres per minute. Thus, the gas flow indicator may only provide an audible sound when gas is flowing at 3 litres per minute. This would therefore help staff to determine that the correct flow rate had been selected. It might also help to ensure that gas is not wasted by employing a higher than necessary flow rate. Consequently, running costs could be reduced.

In particular embodiments, the first inlet may pass orthogonally through the second inlet. In which case, the gas flow indicator may be located in the path of gas flowing through the first inlet and in the path of gas flowing though the second inlet. Accordingly, the inhalation and/or exhalation of a patient's breath may affect (e.g. interrupt or slow) the audible sound produced by the gas flow indicator so that it may also be possible to detect a patient's breathing by the variation of the audible sound.

In further embodiments, the medical equipment may be constituted by a breathing mask. The breathing mask may be of the type commonly used for patients in recovery wards. The breathing mask may be configured for supplying air/oxygen provided through at least one inlet to a patient. The gas flow indicator may be provided in the at least one inlet and may be arranged to provide an audible indication when gas is correctly flowing into the mask (i.e. when the patient is inhaling). Alternatively or additionally, the gas flow indicator may be configured to provide an audible indication when gas is correctly flowing out of the mask (i.e. when the patient is exhaling). Thus, in embodiments of the invention, the gas flow indicator may generate a rhythmical sound in response to a patient's breathing. In this instance, it is envisaged that the gas flow indicator may be selectively coupled to a standard breathing mask when required. Alternatively, the staff on each ward may have access to one supply of masks without gas flow indicators and another supply of masks including gas flow indicators so that they can select which type of mask to use with any given patient. In either case, the staff may choose to use a mask with a gas flow indicator only when they deem it necessary to monitor a particular patient's breathing. This is advantageous since it may be difficult to identify an individual patient having problems breathing if a number of people on the same ward are all provided with masks generating noises associated with their breathing.

A second aspect of the present invention concerns the use of a gas flow indicator according to the first aspect of the invention to indicate that gas is flowing through medical equipment.

Further aspects of the present invention include: a piece of medical equipment including a gas flow indicator according to the first aspect of the invention; a respiratory care device including a gas flow indicator according to the first aspect of the invention; an airway management device including a gas flow indicator according to the first aspect of the invention; a heat moisture exchanger including a gas flow indicator according to the first aspect of the invention; an oxygen enrichment device including a gas flow indicator according to the first aspect of the invention; and a breathing mask including a gas flow indicator according to the first aspect of the invention.

The optional features described above in relation to the first aspect of the present invention apply also to the second and further aspects of the invention, where applicable.

BRIEF DESCRIPTION OF THE DRAWINGS

Specific embodiments of the various aspects of the present invention are described in more detail below in relation to the accompanying drawings, in which.

DETAILED DESCRIPTION OF CERTAIN EMBODIMENTS

Figure 1:
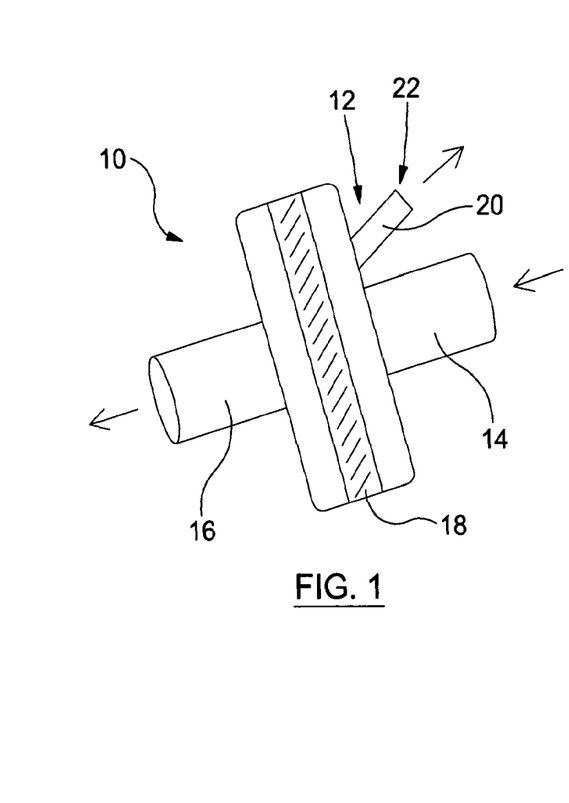
FIG. 1 illustrates a first embodiment of the present invention in which a gas flow indicator is incorporated into an HME.

With reference to FIG. 1, there is illustrated a heat moisture exchanger (HME) 10 comprising a gas flow indicator 12 in accordance with a first embodiment of the present invention. The heat moisture exchanger 10 comprises a cylindrical inlet 14 for connection to a gas supply, a cylindrical outlet 16 for connection to an endotracheal tube or laryngeal mask, and a filter 18 therebetween. The filter 18 is configured to trap heat and moisture on exhalation and to return heat and moisture on inhalation.

A cylindrical sampling port 20 is provided adjacent the inlet 14 and, in this instance, the gas flow indicator 12 is housed within the sampling port 20 and is configured to provide an audible indication when gas is exiting the HME 10 through the sampling port 20 and into the atmosphere.

It will be understood that the HME 10 is configured as a single use disposable item to avoid the need for sterilisation between subsequent uses.

In use, the inlet 14 is connected to an anaesthetic machine for the delivery of anaesthetic gas to a patient and the outlet 16 is connected to an endotracheal tube or laryngeal mask fitted on the patient. The sampling port 20 may be connected to monitoring equipment or may be closed by a cap when not required. However, if nothing is connected to a free end 22 of the sampling port 20 (i.e. it is not connected to further equipment or close off by a cap), gas entering the HME 10 will escape into the atmosphere and this will cause the gas flow indicator 12 to generate an audible sound, thereby alerting persons close by that there is a problem. Accordingly, the gas flow indicator 12 will serve as a safety mechanism to alert personnel that gas (in this case, anaesthetic gas) is escaping and therefore the patient may not be receiving gases as intended.

Figure 2A:
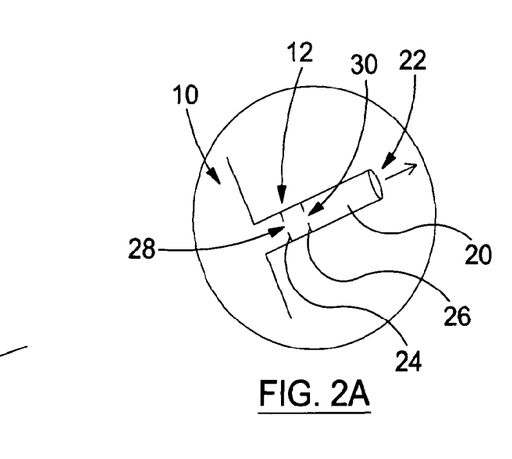
FIG. 2A shows an enlarged cross-sectional view of the sampling port of the HME of FIG. 1, showing the whistling means therein.

FIG. 2A shows the structure of the gas flow indictor 12 in situ within the sampling port 20. Thus, it can be seen that the gas flow indicator 12 comprises a whistling means provided by a first transverse baffle 24 and a second transverse baffle 26, spaced from the first baffle 24 and closer to the free end 22 of the sampling port 20 than the first baffle 24. The first baffle 24 has a first aperture 28 disposed centrally therethrough and the second baffle 26 has a second aperture 30 disposed centrally therethrough. In this embodiment, the first and second apertures 28, 30 are constituted by circular holes of the same diameter. However, in other embodiments the first and second apertures 28, 30 may be constituted by holes of other shapes and each may comprise different dimensions.

It will be understood that, in use, gas flowing through the sampling port 20 towards the free end 22 will be forced through the narrow apertures 28, 30 in the baffles 24, 26 before being allowed to exit through the free end 22 and this flow of gas will therefore produce an audible whistling sound. However, if the free end 22 is closed by a cap there will be no flow of gas through the sampling port 20 (i.e. the gas will be relatively static within the sampling port 20) and so no sound will be generated. Similarly, when the free end 22 is connected to further equipment, the gas flowing through the sampling port 20 will be reduced to a very low flow rate thereby either limiting or preventing an audible sound from being generated.

Figure 2B:
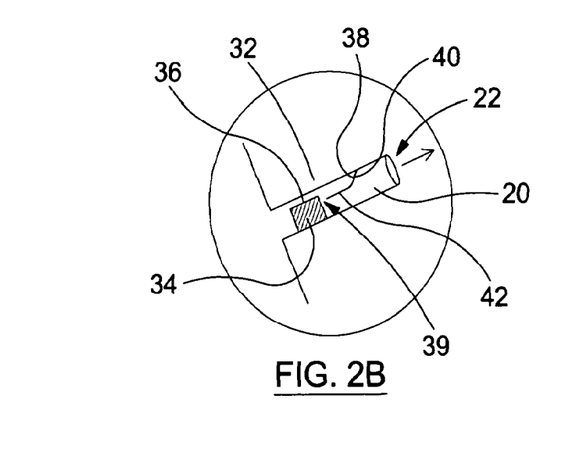
FIG. 2B shows an enlarged cross-sectional view of the sampling port of the HME of FIG. 1, having an alternative whistling means therein.

FIG. 2B shows an alternative gas flow indicator 32 that may be situated within the sampling port 20. The gas flow indicator 32 comprises an occlusion 34 in the form of a generally cylindrical solid plug which is configured to mate with an inner surface of the sampling port 20 along a base and substantially around side portions of the sampling port 20 but which has a cut-out along a top surface to allow gases to flow along a narrow passageway between the top 36 of the occlusion 34 and the sampling port 20. A deflector 38 is provided between the occlusion 34 and the free end 22 to deflect gases flowing over the top 36 of the occlusion 34 back towards the occlusion and through a narrow gap 39 between the occlusion 34 and the deflector 38. The deflector 38 comprises a first portion 40 angled upwardly towards the free end 22 of the sampling port 20, the upper end of which is in contact with the top surface of the sampling port 20 and the lower end of which is disposed at a height slightly below the top 36 of the occlusion 34, and a horizontal portion 42 which extends from the lower end of the first portion 40 and which terminates close to the occlusion 34 to provide the narrow gap 39 therebetween.

In use, the gas flow indicator 32 will generate an audible whistling sound when gas is forced to flow through the narrow gap 39 before exiting the sampling port 20.

In the arrangements shown in FIGS. 2A and 2B, it will be clear that the gas flow indicators 12 and 32 are integrally formed within the sampling port 20. However, in other embodiments, the gas flow indicators 12 and 32 may be formed as discrete components for insertion into a device such as an HME.

Figure 3A:
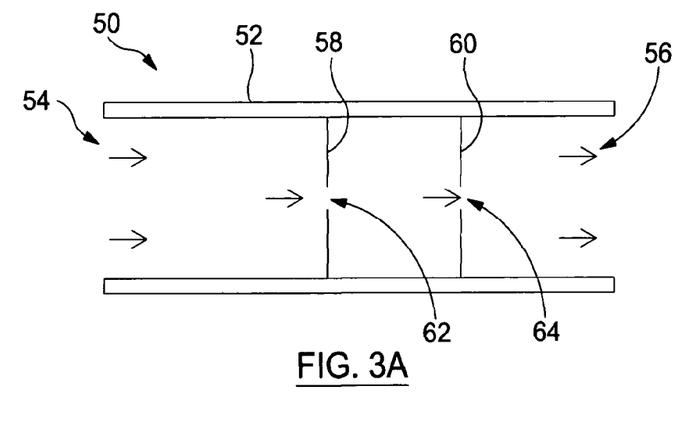
FIG. 3A shows an enlarged cross-sectional view of the whistling means illustrated in FIG. 2A but configured as a discrete gas flow indicator.

One such discrete gas flow indicator 50 is shown in FIG. 3A and comprises a cylindrical body 52 having a first end 54 and a second end 56, the body 52 housing the whistling means described above in relation to FIG. 2A. Thus, the gas flow indicator 50 comprises a first transverse baffle 58 and a second transverse baffle 60, spaced from the first baffle 58 and closer to the second end 56 than the first baffle 58. The first baffle 58 has a first aperture 62 disposed centrally therethrough and the second baffle 60 has a second aperture 64 disposed centrally therethrough. As described previously, the first and second apertures 62, 64 are constituted by circular holes of the same diameter. However, in other embodiments the first and second apertures 62, 64 may be constituted by holes of other shapes and each may comprise different dimensions. As per the gas flow indicator 12, in use, gas flowing through the body 52 towards the second end 56 will be forced through the narrow apertures 62, 64 before being allowed to exit through the second end 56 and this flow of gas will produce an audible whistling sound.

Figure 3B:
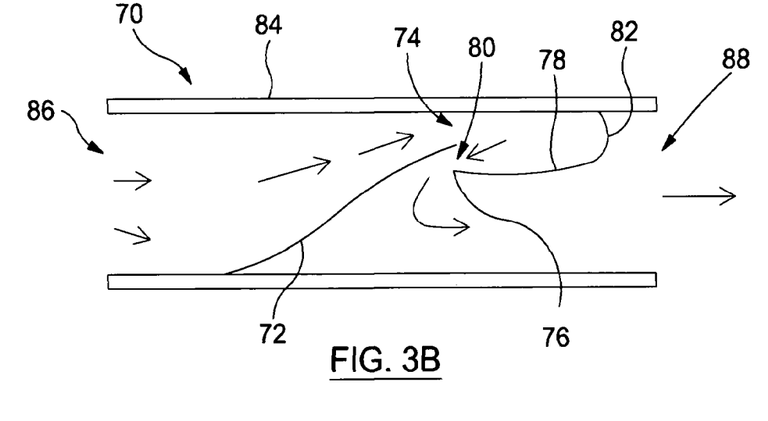
FIG. 3B shows an enlarged cross-sectional view of an alternative whistling means configured as a discrete gas flow indicator.

FIG. 3B shows an alternative discrete gas flow indicator 70 comprising a whistling means similar to that described above in relation to FIG. 2A but wherein the occlusion is now constituted by a thin aerofoil 72 shaped to smoothly deflect gases upwardly and through a narrow passageway 74. In this case, the upper end of the curved aerofoil 72 is vertically spaced from a free end 76 of a deflector 78 so as form a vertical narrow gap 80 therebetween. The deflector 78 is similar to that described above although in this case the first portion 82 is substantially concave rather than sloped upwardly. As above, the whistling means is housed in a cylindrical body 84 having a first end 86 and a second end 88. In use, gas may flow in through the first end 86, be deflected upwardly by the aerofoil 72 through the passageway 74 and towards the deflector 78 where it is then reflected by the first portion 82 and forced backwards and through the narrow gap 80. The gas will then be reflected once more by the smooth under-surface of the aerofoil 72 in order to exit through the second end 88. As above, the gas flow indicator 70 will generate an audible whistling sound when the gas is forced to flow through the narrow gap 80 before exiting the second end 88.

Figure 4:
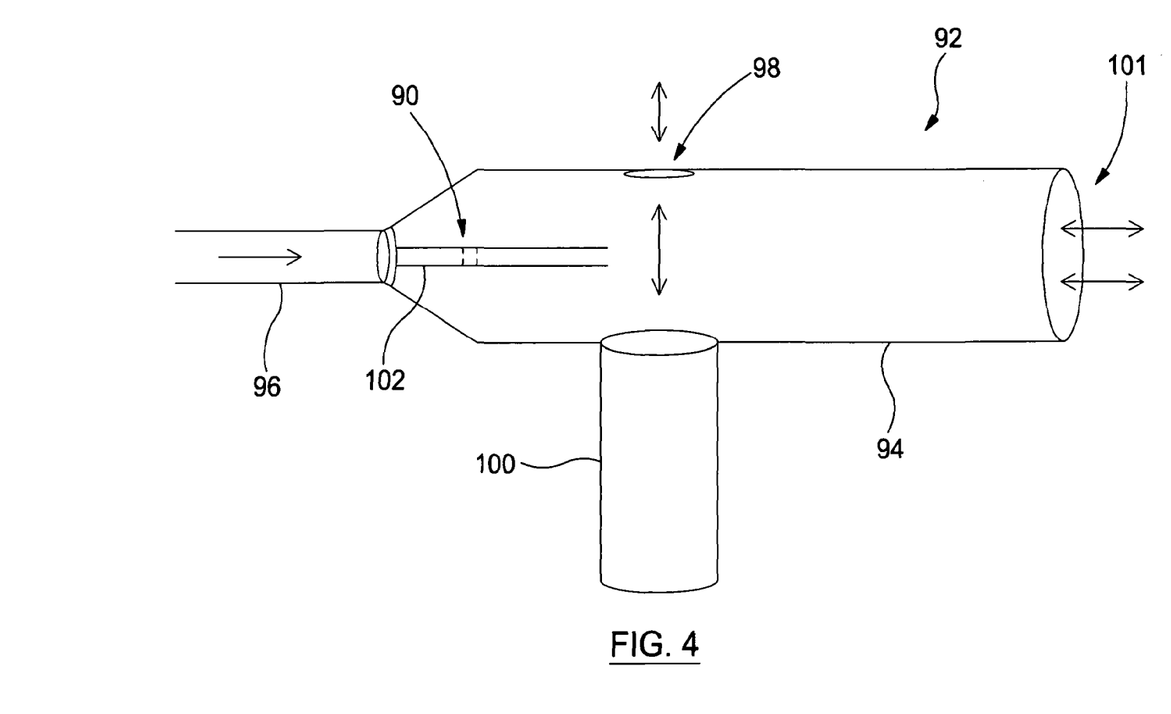
FIG. 4 shows a second embodiment of the present invention in which a gas flow indicator is incorporated into a rigid oxygen enrichment device.

FIG. 4 shows a second embodiment of the present invention in which a gas flow indicator 90 is incorporated into a rigid oxygen enrichment device 92. The oxygen enrichment device 92 comprises a generally cigar-shaped reservoir 94 configured to receive oxygen flowing from an oxygen cylinder through a first inlet 96, a second inlet 98 which is open to the air and a patient outlet 100 which connects to a patient via a suitable tube or mask and which is arranged to provide a mixture of air and oxygen to the patient through the tube or mask. The reservoir 94 has an open end 101, opposite to the first inlet 96, which allows excess gas to flow out of the device 92. On inspiration, the first part of the breath will mainly comprise oxygen from within the reservoir 94 and the second part of the breath will mainly comprise air from the open end 101 and the second inlet 98.

The gas flow indicator 90 is located in path of the first inlet 96 although it is actually disposed in an extension 102 to the first inlet 96 which is provided within the body of the reservoir 94. In this embodiment, the gas flow indicator 90 comprises the whistling mechanism described above in relation to FIG. 2A. Accordingly, the gas flow indicator 90 is arranged to provide an audible indication when oxygen is correctly flowing from the cylinder into the reservoir 94. As such, the lack of an audible sound will indicate that there is a problem with the oxygen supply and consequently the patient may not be receiving the gases intended. This may be caused by cylinder being empty or the cylinder may not have been turned on. The lack of sound can therefore be used to alert personnel to check the status of the oxygen supply.

In addition to the above, the gas flow indicator 90 is configured only to provide an audible sound when gas is flowing at a pre-determined flow rate so as to provide a patient with a 50% mixture of air and oxygen. Accordingly, the lack of an audible sound may also indicate that the correct flow rate has not been achieved. This is can be useful in minimising waste and thereby saving costs by ensuring that a higher than required flow rate is not inadvertently employed.

Figure 5:
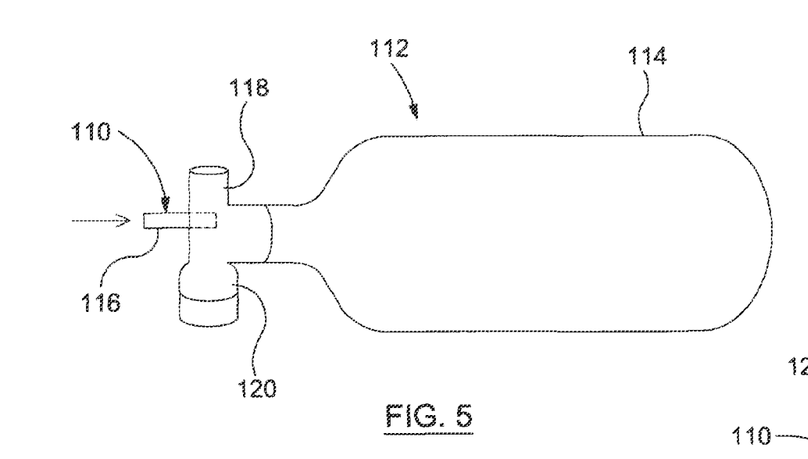
FIG. 5 shows a third embodiment of the present invention in which a gas flow indicator is incorporated into a flexible oxygen enrichment device.

FIG. 5 shows a third embodiment of the present invention in which a gas flow indicator 110 is incorporated into an oxygen enrichment device 112 which is similar to that shown in FIG. 4 but wherein the reservoir is constituted by a flexible bag 114. The oxygen enrichment device 112 therefore comprises an elongate bag reservoir 114 configured to receive oxygen flowing from an oxygen cylinder through a first inlet 116, a second inlet 118 which is open to the air and an outlet 120 arranged to provide a mixture of air from the second inlet 118 and oxygen from the reservoir 114 to a patient through a suitable tube or mask.

Figure 6:
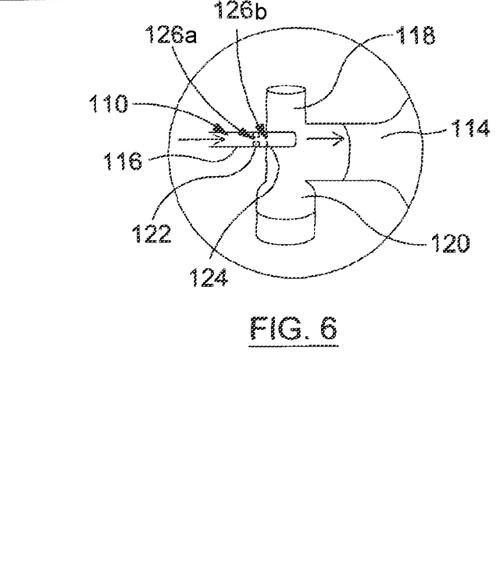
FIG. 6 shows an enlarged part cross-sectional view of an inlet of the flexible oxygen enrichment device of FIG. 5, illustrating the whistling means therein.

As shown in FIG. 6, the gas flow indicator 110 is located in path of the first inlet 116 before the path of the first inlet 116 crosses the path between the second inlet 118 and the outlet 120. In other embodiments, the gas flow indicator 110 may be located in the path of gas flowing through the first inlet 116 and in the path of gas flowing through the second inlet 118 so that the inhalation and/or exhalation of a patient's breath can interrupt the audible sound produced by the gas flow indicator 110 thereby making it possible to detect a patient's breathing by the variation of the audible sound.

In the particular embodiment shown in FIG. 6, the gas flow indicator 110 comprises the whistling mechanism similar to that described above in relation to FIG. 2A although, in this case, the first baffle 122 has a greater thickness than the second baffle 124. First and second apertures 126a and 126b are still provided through each respective baffle 122, 124 to generate an audible indication when oxygen is correctly flowing from the cylinder into the reservoir 114. Thus, as above, the lack of an audible sound will indicate that there is a problem with the oxygen supply and that, the patient may not be receiving the gases intended.

Figure 7:
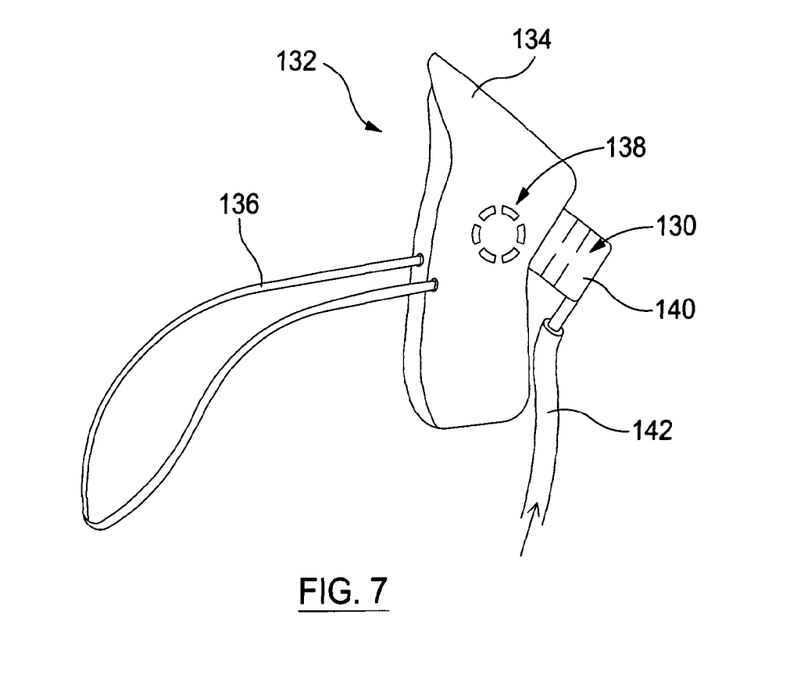
FIG. 7 shows a fourth embodiment of the present invention in which a gas flow indicator is incorporated into a breathing mask.

FIG. 7 shows a fourth embodiment of the present invention in which a gas flow indicator 130, comprising a whistling mechanism as described above in relation to FIG. 2A, is incorporated into a breathing mask 132. The breathing mask 132 comprises a mask body 134 designed to fit over a patient's mouth and nose when in use. A flexible strap 136 is provided to wrap around a patient's head to hold the mask body 134 in a close relationship with the patient's face. Each side of the mask body 134 is provided with discontinuous circular aperture 138 to allow air and other gases to flow into and out of the mask body 134 when in use.

In the embodiment shown in FIG. 7, the gas flow indicator 130 is provided in an inlet port 140 configured to be connected to an oxygen supply through tubing 142. Accordingly, the patient can be supplied with oxygen through the inlet port 140 and air through the circular apertures 138. When oxygen is being supplied to the patient through the inlet port 140, the gas flow indicator 130 will provide an audible indication that gas is flowing. In addition, the sound generated by the gas flow indicator 130 may be interrupted by the patient's breathing. Furthermore, when no oxygen is being supplied to the patient, the patient's breathing may cause the gas flow indictor 130 to generate a sound. Accordingly, the breathing mask 132 can be configured such that the gas flow indicator 130 generates an audible sound in response to selected conditions.

In some embodiments, the gas flow indicator 130 may be configured so that it can be disabled or removed by medical staff so that the device in which the gas flow indicator 130 is provided (e.g. an oxygen delivery device) can function without the gas flow indicator function. Furthermore, the volume of the sound created by the gas flow indicator 130 may be adjustable.

It is noted that embodiments of the present invention comprise any oxygen enrichment device having a gas flow indicator that produces a sound to indicate when oxygen is flowing through the device. The device may be further configured such that the sound is interrupted by a patient's breathing. Moreover, the device may be configured such that it can be reverted or changed into a traditional oxygen enrichment device by disabling or removing the oxygen flow indicator.

It will be appreciated by persons skilled in the art that various modifications may be made to the above embodiments without departing from the scope of the present invention.

What is claimed is:

1. A breathing mask for monitoring breathing of a patient, the breathing mask comprising:
    a mask body arranged to fit over a patient's nose and mouth, the mask body having an inlet port configured to be connected to a supply of air or a mixture of air and oxygen transmitted through a gas flow path to a patient and an aperture to allow passage of the patient's breath from the mask; and
    a gas flow indicator comprising a body and an occlusion, the body defining a passage having an inlet and an outlet, the occlusion extending from the body into the passage, the inlet connected to the supply of air or mixture of air and oxygen, wherein, during use, the gas flow indicator is disposed in the gas flow path whereby the occlusion is arranged to force gas through a narrow opening in the body to provide an audible indication when gas is correctly flowing from the supply into the breathing mask and further the gas flow indicator is disposed in the flow path of the patient's breath and configured so that the audible indication is silenced during an exhale portion of the patient's breathing cycle.

2. The breathing mask according to claim 1 configured such that the presence of an audible sound signals correct gas flow and the absence of an audible sound signals incorrect gas flow.

3. The breathing mask according to claim 1 wherein the breathing mask is configured for respiratory care or airway management.

4. The breathing mask according to claim 1, wherein the breathing mask is configured to be disposed close to a patient's air inlet so as to indicate if there is a problem with the gases getting to the patient.

5. The breathing mask according to claim 1 configured as a disposable device.

6. The breathing mask according to claim 1 wherein the occlusion comprises a blade configured to bisect a flow of gas, thereby creating a turbulent vortex which causes the gas to vibrate to make an audible sound.

7. The breathing mask according to claim 1 wherein the body defines a chamber in which gas resonates.

8. The breathing mask according to claim 7 wherein the chamber is configured such that gas resonates therein at a pre-determined frequency.

9. The breathing mask according to claim 1 wherein the inlet port is configured to connect to a tube from a source of the supply of air or mixture of air and oxygen.

10. The breathing mask according to claim 1 wherein the body is a cylindrical body.

11. The breathing mask according to claim 1 wherein the occlusion includes:
    a first transverse baffle extending from the body into the passage, the first transverse baffle defining a first aperture; and
    a second transverse baffle extending from the body into the passage and spaced apart from the first transverse baffle, the second transverse baffle defining a second aperture.

12. The breathing mask according to claim 11 wherein the first aperture is disposed centrally within the first transverse baffle and the second aperture is disposed centrally within the second transverse baffle.

13. The breathing mask according to claim 11 wherein the first aperture and the second aperture each are circular and have equal diameters.

14. The breathing mask according to claim 1 wherein the occlusion includes:
    an aerofoil having an aerofoil free end and extending from the body into the passage; and
    a deflector having a deflector free end and extending from the body, the aerofoil free end located proximate the deflector free end to form a narrow gap.

15. The breathing mask according to claim 14 wherein the deflector has a concave shape and is arranged such that the gas flow path reverses direction after contacting the deflector.

16. A breathing mask comprising:
    a mask body sized to fit over a nose and a mouth of a patient, the mask body defining an inlet port and an aperture, the aperture sized to allow passage of a breath of the patient from the mask; and
    a gas flow indicator including a cylindrical body and an occlusion comprising an aerofoil having an aerofoil free end and extending from the cylindrical body into a passage of said cylindrical body and a deflector having a deflector free end also extending from the cylindrical body into said passage,
        wherein the aerofoil free end is located proximate the deflector free end to form a narrow gap,
        wherein the deflector free end is arranged such that the gas flow path reverses direction after contacting the deflector; and
        wherein the cylindrical body defining said passage having an inlet and an outlet, the outlet connected to the inlet port, the inlet configured to connect a gas supply such that, during use, a gas flows from the gas supply through the narrow gap of the gas flow indicator to the patient providing an audible indication and during an exhale portion of a breathing cycle, the audible indication is silenced.

17. The breathing mask according to claim 16 wherein the occlusion includes:
    a first transverse baffle extending from the cylindrical body into the passage, the first transverse baffle defining a first aperture; and
    a second transverse baffle extending from the cylindrical body into the passage and spaced apart from the first transverse baffle, the second transverse baffle defining a second aperture.

18. The breathing mask according to claim 17 wherein the first aperture is disposed centrally within the first transverse baffle and the second aperture is disposed centrally within the second transverse baffle, and wherein the first aperture and the second aperture each are circular and have equal diameters.

\* \* \* \* \*